United States Patent [19]

Jendralla et al.

[11] Patent Number: 5,166,171
[45] Date of Patent: Nov. 24, 1992

[54] 6-PHENOXYMETHYL-4-HYDROXYTETRAHYDROPYRAN-2-ONES AND 6-THIPHENOXYMETHYL-4-HYDROXYTETRAHYDROPYRAN-2-ONES AND THE CORRESPONDING DIHYDROXYCARBOXYLIC ACID DERIVATIVES, SALTS AND ESTERS, AND IN TREATING HYPERCHOLESTEROLEMIA

[75] Inventors: Heiner Jendralla, Frankfurt am Main; Günther Wess, Erlensee; Wilhelm Bartmann, Bad Soden am Taunus; Gerhard Beck, Frankfurt am Main, all of Fed. Rep. of Germany

[73] Assignee: Hoechst Aktiengesellschaft, Frankfurt am Main, Fed. Rep. of Germany

[21] Appl. No.: 680,613

[22] Filed: Apr. 2, 1991

Related U.S. Application Data

[63] Continuation of Ser. No. 350,428, May 11, 1989, abandoned.

[30] Foreign Application Priority Data

May 13, 1988 [DE] Fed. Rep. of Germany .... 38-16-388
Jun. 11, 1988 [DE] Fed. Rep. of Germany .... 38-19-999

[51] Int. Cl.$^5$ ...................... A61K 31/37; C07D 30/10
[52] U.S. Cl. .................................. 514/460; 549/292; 560/17; 560/59; 562/469; 562/470; 514/532; 514/533; 514/543; 514/568; 514/824
[58] Field of Search ................ 549/292; 514/460, 533, 514/543, 532, 824, 568; 560/11, 59, 17; 562/470, 469

[56] References Cited

U.S. PATENT DOCUMENTS 4,459,422 7/1984 Willard et al. ...................... 549/292

FOREIGN PATENT DOCUMENTS 0216127 4/1987 European Pat. Off. ............ 549/292
3632893 4/1988 Fed. Rep. of Germany ...... 549/292

OTHER PUBLICATIONS

G. E. Stokker, et al., *J. Med. Chem.*, "3-Hydroxy-3-methylglutaryl-Coenzyme A Reductase Inhibitors," 28 (3), pp. 347-358, (1985).
Bartmann, W., Chemical Abstracts 109:128,826k, abstract of DE 3,632,893 A1, (1988).
Wess, G., et al., Derwent Abstract of EP 216,127 (1987).
G. E. Stokker et al., 3-Hydroxy-3-methylglutaryl-coenzyme A Reductase Inhibitors 3, 7-(3,5-Disubstituted [1,1'-biphenyl]-2-yl)-3,5-dihydroxy-6-heptenoic Acids and Their Lactone J. Med. Chem. 1986, 29, 170-181.
G. E. Stokker et al., 3-Hydroxy-3-methylglutaryl-coenzyme A Reductase Inhibitors, 5,6-(Fluoren-9-yl)- and 6-(Fluoren-9-ylodenyl)-3,5-dihydroxyhexanoic Acids and Their Lactone Derivatives, J. Med. Chem. 1986, 29, 852-855.
W. F. Hoffman et al., 3-Hydroxy-3-methylglutaryl-coenzyme A Reductase Inhibitors, 2, Structural Modification of 7-(Substituted aryl)-3,5-dihydroxy-6-heptenoic Acids and Their Lactone Derivatives, J. Med. Chem. 1986, 29, 159-169.
N. Nakaya et al., The Effect of CS-514, an Inhibitor of HMG-CoA Reductase, on Serum Lipids in Healthy Volunteers Atherosclerosis, 1986, 61, 125-128.
Eptastatin Sodium, Drugs of the Future, 1987, 12, 437-442.
M. J. T. M. Mol et al., Effects of Synvinolin (MK-733) on Plasma Lipids in Familial Hypercholesterolaemia, The Lancet, Oct. 25, 1986, 936-939.
A. G. Olsson et al., Synvinolin in Hypercholesterolaemia Culture, The Lancet, Aug. 16, 1986, 390-391.
A. S. Pappu et al., Divergent Response of Plasma Mevalonate to Mevinlon Normal and Familial Hypercholesterolemic Subjects Clinical Research, 34, 1986, 684A.
Akira Endo, Compactin (ML-236B) and Related Compounds as Potential Cholesterol-Lowering Agents That Inhibit HMG-CoA Reductase, J. Med. Chem. 1985, 28, 401-405.

Primary Examiner—Richard L. Raymond
Assistant Examiner—Mark W. Russell
Attorney, Agent, or Firm—Finnegan, Henderson Farabow, Garrett and Dunner

[57] ABSTRACT

6-Phenoxymethyl-4-hydroxytetrahydropyran-2-ones and 6-thiophenoxymethyl-4-hydroxytetrahydropyran-2-ones and the corresponding dihydroxycarboxylic acid derivatives, salts and esters, processes for the preparation of these compounds, their use as pharmaceuticals, pharmaceutical preparations and novel phenols and thiophenols Compounds of the general formula I

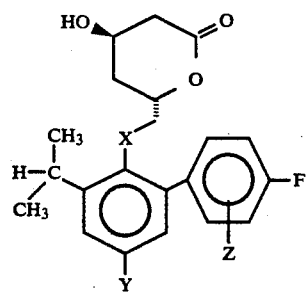

and the corresponding open-chain dihydroxycarboxylic acids of the formula II (Abstract continued on next page.)

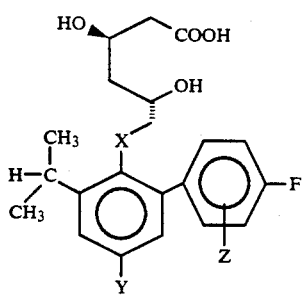

in which X, Y and Z have the meanings given, and pharmacologically tolerated salts thereof with bases and pharmacologically tolerated esters thereof, processes for the preparation of these compounds, their use as pharmaceuticals and pharmaceutical preparations are described. Novel phenols and thiophenols of the formula III

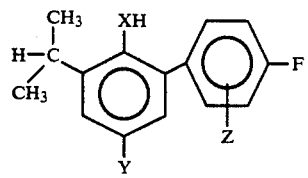

in which X, Y and Z have the meanings given, are also described.

4 Claims, No Drawings

6-PHENOXYMETHYL-4-HYDROXYTETRAHYDROPYRAN-2-ONES AND 6-THIPHENOXYMETHYL-4-HYDROXYTETRAHYDROPYRAN-2-ONES AND THE CORRESPONDING DIHYDROXYCARBOXYLIC ACID DERIVATIVES, SALTS AND ESTERS, AND IN TREATING HYPERCHOLESTEROLEMIA

This application is a continuation of application Ser. No. 07/350,428, filed May 11, 1989, now abandoned.

DESCRIPTION

The enzyme 3-hydroxy-3-methylglutaryl-coenzyme A reductase (HMG-CoA-reductase) plays a central role in the biosynthesis of cholesterol [A. Endo, J. Med. Chem. 28, 401 (1985)]. Inhibitors of this enzyme, in particular mevinolin [A.S. Pappu et al., Clin. Res. 34, 684 A (1986)], synvinolin [A.S. Olsson et al., The Lancet, 391 (1986); and M.J.T.M. Mol et al., The Lancet, 936 (1986)] and eptastatin [Drugs of the Future 12, 437 (1987); and N. Nakaya et al. Atherosclerosis 61, 125 (1986)] have been clinically tested for the treatment of hypercholesterolemics. Structurally simplified completely synthetic analogs of these compounds have been described [G.E. Stokker et al., J. Med. Chem. 29. 170 and 852 (1986), W.F. Hoffman et al., J. Med. Chem. 29, 159 (1986)].

European Patent Application A-0,216,127 (corresponding to U.S. patent application No. 900,848) claims compounds of the formula Ia

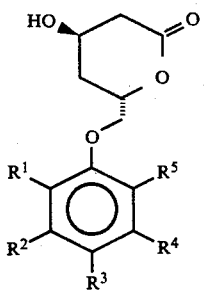

Ia wherein $R^1$ and $R^5$ are identical or different and denote a) hydrogen or halogen, b) cycloalkyl having 4–8 carbon atoms or a phenyl radical which can be substituted in the nucleus by 1 to 3 substituents from the group comprising halogen, trifluoromethyl and/or alkyl or alkoxy having in each case 1–4 carbon atoms or c) a straight-chain or branched alkyl radical having 1 to 18 carbon atoms or a straight-chain or branched alkenyl radical having 2 to 18 carbon atoms, it being possible for the alkyl and alkenyl radicals in turn to be substituted by 1 to 3 substituents from the group comprising α) straight-chain or branched alkoxy radicals having up to 10 carbon atoms or cycloalkoxy radicals having 3 to 7 carbon atoms or straight-chain or branched alkenyloxy or alkynyloxy radicals having 3 to 6 carbon atoms, β) halogen, hydroxyl, cycloalkyl having 3–7 carbon atoms, and unsubstituted phenyl or α- or β-thienyl radicals, or phenyl α- or β-thienyl radicals which are in turn substituted in the nucleus by 1 to 3 substituents from the group comprising halogen, trifluoromethyl and/or alkyl or alkoxy having 1–4 carbon atoms, γ) unsubstituted phenoxy, benzyloxy or α- or β-thienyloxy radicals, or phenoxy, benzyloxy α- or β-thienyloxy radicals which are in turn substituted in the nucleus by 1 to 3 substituents from the group comprising halogen, trifluoromethyl and/or alkyl or alkoxy having 1 to 4 carbon atoms, and δ) the group

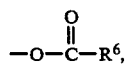

wherein $R^6$ denotes: a straight or branched alkyl or alkenyl radical having up to 8 carbon atoms, or a cycloalkyl or cycloalkenyl radical having in each case 3–8 carbon atoms, or an unsubstituted phenyl radical, or a phenyl radical which is in turn substituted in the nucleus by 1 to 3 substituents from the group comprising halogen, trifluoromethyl and/or alkyl or alkoxy having 1–4 carbon atoms, or a 3-pyridyl radical, $R^2$ and $R^4$ are identical or different and denote hydrogen, alkyl having 1–4 carbon atoms, halogen or alkoxy having 1–4 carbon atoms, and $R^3$ is hydrogen, alkyl or alkenyl having up to 4 carbon atoms, halogen or alkoxy having 1–4 carbon atoms, and the corresponding open-chain dihydroxycarboxylic acids, pharmacologically tolerated salts thereof with bases and pharmacologically tolerated esters thereof.

The compounds described in this Application inhibit HMG-CoA reductase with $IC_{50}$ values in the $10^{-5}$ to $10^{-8}$ molar range. According to the data in the description, the most potent compound Ia ($R^1=R^3=Cl$, $R^2=R^4=H$,

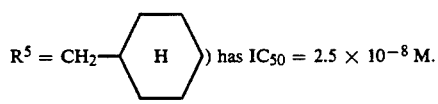

German Offenlegungsschrift 3,632,893 (=Derwent Abstract 88–99 366/15) relates inter alia to compounds of the general formula Ib

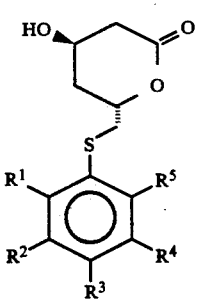

Ib in which $R^1$ and $R^5$ are identical or different and denote a) hydrogen or halogen b) a phenyl radical which can be substituted in the nucleus by 1 to 3 substituents from the group comprising halogen, trifluoromethyl, methyl, ethyl, methoxy and ethoxy, c) an alkyl radical having 1-5 carbon atoms, which can be substituted by 1 to 3 substituents from the group comprising
  α) $C_1$-$C_3$-alkoxy radicals or cycloalkoxy radicals having 3 to 7 carbon atoms,
  β) phenoxy or benzyloxy radicals which can in turn be substituted in the nucleus by 1 to 3 substituents from the group comprising halogen, trifluoromethyl, methyl, ethyl, methoxy and ethoxy,
  γ) halogen cycloalkyl having 3-carbon atoms or phenyl radicals which can in turn be substituted in the nucleus by 1 to 3 substituents from the group comprising halogen, trifluoromethyl, methyl, ethyl, isopropyl, methoxy and ethoxy, and
  δ)

$$O-\underset{\underset{O}{\|}}{C}\text{-alkyl}$$

groups with a total of 3-8 carbon atoms, $R^2$ and $R^4$ are identical or different and denote hydrogen, halogen, methyl, ethyl, methoxy, ethoxy or benzyloxy and $R^3$ is hydrogen, halogen, trifluoromethyl, methyl, ethyl, methoxy or ethoxy, and the corresponding open-chain dihydroxycarboxylic acids, pharmacologically tolerated salts thereof with bases and pharmacologically tolerated ester thereof.

According to the data in this Application, the compounds of the formula Ib described are as a rule slightly less potent than Ia for the same substitution pattern $R^1$-$R^5$.

Substitution patterns ($R^1$ to $R^5$) which are not described by examples in these Applications have now been found, surprisingly, which impart to the compounds of the general formulae Ia and Ib an activity which is up to one power of ten greater than the best examples listed in EP-A-0,216,127 and DE-A-3,632,893. The substitution patterns in respect of substituents $R^1$, $R^2$, $R^4$ and $R^5$ lie completely within and those with respect of R: lie only partly within the general patent claims of EP-A-0,216,127 and DE-A-3,632,893, since it has furthermore been found that $R^3$ can also have meanings which are not described in the two previous Applications.

The invention relates to novel compounds of the general formula I and the corresponding open-chain dihydroxycarboxylic acids of the formula II pharmacologically tolerated salts thereof with bases and pharmacologically tolerated esters thereof. In the formulae, X denotes oxygen or sulfur,
Y denotes
  a) a straight-chain or branched alkyl radical having 3 to 12 carbon atoms or
  b) cycloalkyl having 3 to 8 carbon atoms or a phenyl radical which ca be substituted in the nucleus by 1 to 3 substituents from the group comprising halogen, trifluoromethyl and/or alkyl or alkoxy having in each case 1 to 4 carbon atoms and
Z denotes hydrogen or a straight-chain or branched alkyl radical having 1 to 4 carbon atoms.

The character of a selection invention is asserted for compounds of the formulae I and II which do not fall within the patent claims of the previous patent applications referred to.

The substituents in the general formulae preferably have the following meanings:
X oxygen
Y isopropyl, tert.-butyl, cyclohexyl, phenyl or p-fluorophenyl
Z hydrogen.

The invention furthermore relates to a process for the preparation of the compounds of the formula I and of the corresponding open-chain dihydroxycarboxylic acids of the formula II, of the pharmacologically tolerated salts thereof with bases and of the pharmacologically tolerated esters thereof. The process comprises
  a) converting correspondingly substituted phenols or thiophenols of the formula III in which X, Y and Z have the meanings given in the case of formulae I and II, with the optically pure iodide of the formula IV in which R[7] denotes a protective group which is stable towards bases and weak acids, into the lactol ether of the formula V

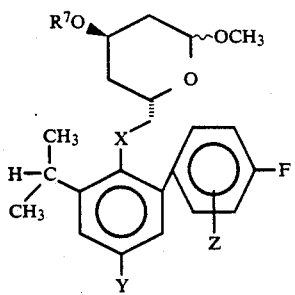

in which X, Y and Z have the meanings given in the case of formulae I and II and R[7] has the meanings given in the case of formula IV, b) hydrolyzing the lactol ethers of the formula V to give the corresponding lactols of the formula VI

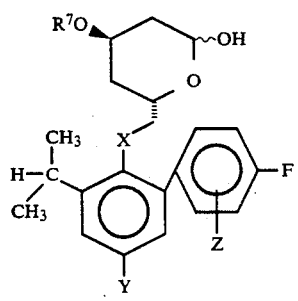

in which X, Y and Z have the meanings given in the case of formulae I and II and R[7] has the meanings given in the case of formula IV, c) oxidizing the lactols of the formula VI to give the corresponding lactones of the formula VII

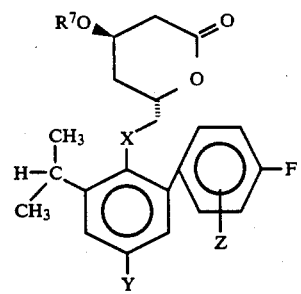

in which X, Y and Z have the meanings given in the case of formulae I and II and R[7] has the meanings given in the case of formula IV, d) converting the resulting protected lactones of the formula VII into compounds of the formula I in a manner which is known per se and, e) if appropriate, converting the resulting compounds of the formula I into the corresponding open-chain dihydroxycarboxylic acids of the formula II, salts thereof or esters thereof, if appropriate converting resulting salts or esters into the free dihydroxycarboxylic acids or, if appropriate, converting the free carboxylic acids into the salts or esters.

The process is advantageously carried out under the conditions which have been described in the previous Applications referred to. The process conditions can be modified according to the meaning of the substituents (cf. for example Embodiment Example 1.8).

The starting compounds of the formula III are novel. The invention therefore also relates to these compounds. The iodides of the formula IV are described, for example, in EP-A-0,216,127.

Syntheses of the phenol and thiophenol units III required are outlined in equation 1 and described below.

Compounds of the formula III can be obtained from 2-isopropylphenol XII or from 2-isopropylphenols XIII substituted in the 4-position by Y by palladium (O)-catalyzed aryl-aryl coupling as the key step. Reviews of palladium (O)-catalyzed aryl-aryl coupling are to be found in E. Negishi, Acc. Chem. Res. 15, 340 (1982) and R.F. Heck "Palladium Reagents in Organic Synthesis", Academic Press (1985), Chapter 6.

According to a recently published strategy (D.A. Widdowson, Y.-Z. Zhang, Tetrahedron 42, 2111 (1986)), aryl Grignard compounds have an increased reactivity in respect of Pd(O)-catalyzed coupling with aryl halides if they carry ortho-alkoxy substituents. If XIII is therefore brominated to give XIV, XIV is then protected with a benzyl group to form XV and the Grignard reagent XVI is formed in THF, this already reacts with the aryl halide XVII (Hal=Br or I) under mild conditions (10° to 65° C.) and under Pd(O)-catalysis to give the coupling product XVIII in outstanding yields (90 to 98%). Removal of the protective group by means of catalytic hydrogenation gives III (X=O). In this strategy, the coupling product III (X=O) is obtained in a very high yield and purity. There is the need to protect the phenolic OH group and subsequently remove the protective group in this process.

Pd(O)-catalyzed aryl-vinyl couplings in the presence of unprotected phenol groups are known (R.F. Heck, Acc. Chem. Res. 12, 146 (1979); C.B. Ziegler Jr., R.F. Heck, J. Org. Chem. 43, 2941 (1978)). This reaction is not completely comparable to aryl-aryl couplings, since no highly basic organometallic reagents (such as the Grignard compound XX) are used therein.

Aryl-aryl couplings in the presence of unprotected phenol groups are novel. This reversal of the conventional strategy described above, that is to say Pd(O)-catalyzed reaction of unprotected ortho-iodophenols XIX with Grignard reagents from p-bromofluorobenzenes XX, has been successfully carried out. One equivalent of XX is consumed for deprotonation of XIX and a further equivalent of XX is consumed for the coupling reaction. Since oligomerization of the Grignard components XX moreover occurs as a side reaction, 2.5 to 3.0 equivalents of XX must be used in order to achieve complete conversion to III (X =O).

It is in this way possible also to carry out quantitative di-couplings on the unprotected diiodide XXI. If 3 equivalents of XX are used, a mixture of the mono-coupling product XIX'

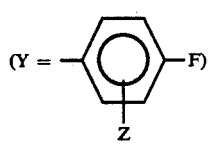

and the di-coupling product III'(Y=

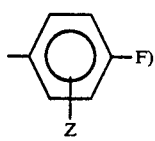

is obtained at room temperature. In contrast, if the ≧4 equivalents of XX are used, the mono-coupling product detectable in the meantime is in the end converted completely into III'. Since this di-coupling reaction takes place without purification of the quite sensitive* diiodide XXI, III'

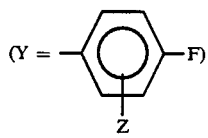

is obtained very directly from XII in an overall yield of 40 to 60% (not optimized!).

*see C.V. Bordlianu, Arch. d. Pharmazie 272, 8 (1934)

This phenol unit III' is advantageously prepared by this process, since in the conventional method the compound XIX' which is in any case formed would have to be used because aryl di-Grignard compounds are unstable [F. Bickelhaupt, Angew. Chem. 99, 1020 (1987)].

Compared with conventional coupling, direct coupling of unprotected iodophenols XIX with aryl Grignard compounds saves two synthesis steps and allows the use of the less expensive fluorobromobenzenes. The price which must be paid is a lower yield of the coupling step.

Tetrakis-(triphenylphosphine)palladium(O), bis(triphenylphosphine)palladium dichloride or a mixture of palladium dichloride and triphenylphosphine has been used as the palladium catalysts. It is known that similar catalyses can also be achieved with nickel-phosphine complexes and related transition metal complexes [see, for example, E. Negishi, Acc. Chem. Res. 15, 340 (1982); J.K. Stille, Angew. Chem. 98, 504 (1986); R.F. Heck, Acc. Chem. Res. 12, 146 (1979); E. Negishi et al., J. Org. Chem. 42, 1821 (1977)].

The thiophenols of the formula III are obtained by methods analogous to those described in the literature from the corresponding phenols of the formula III by reaction with a dialkylthiocarbamoyl chloride, subsequent Newman-Kwart rearrangement by means of heat and reductive cleavage of the S-aryldialkylthiocarbamates formed to give thiophenols of the formula III (cf. also DE-A-3,632,893).

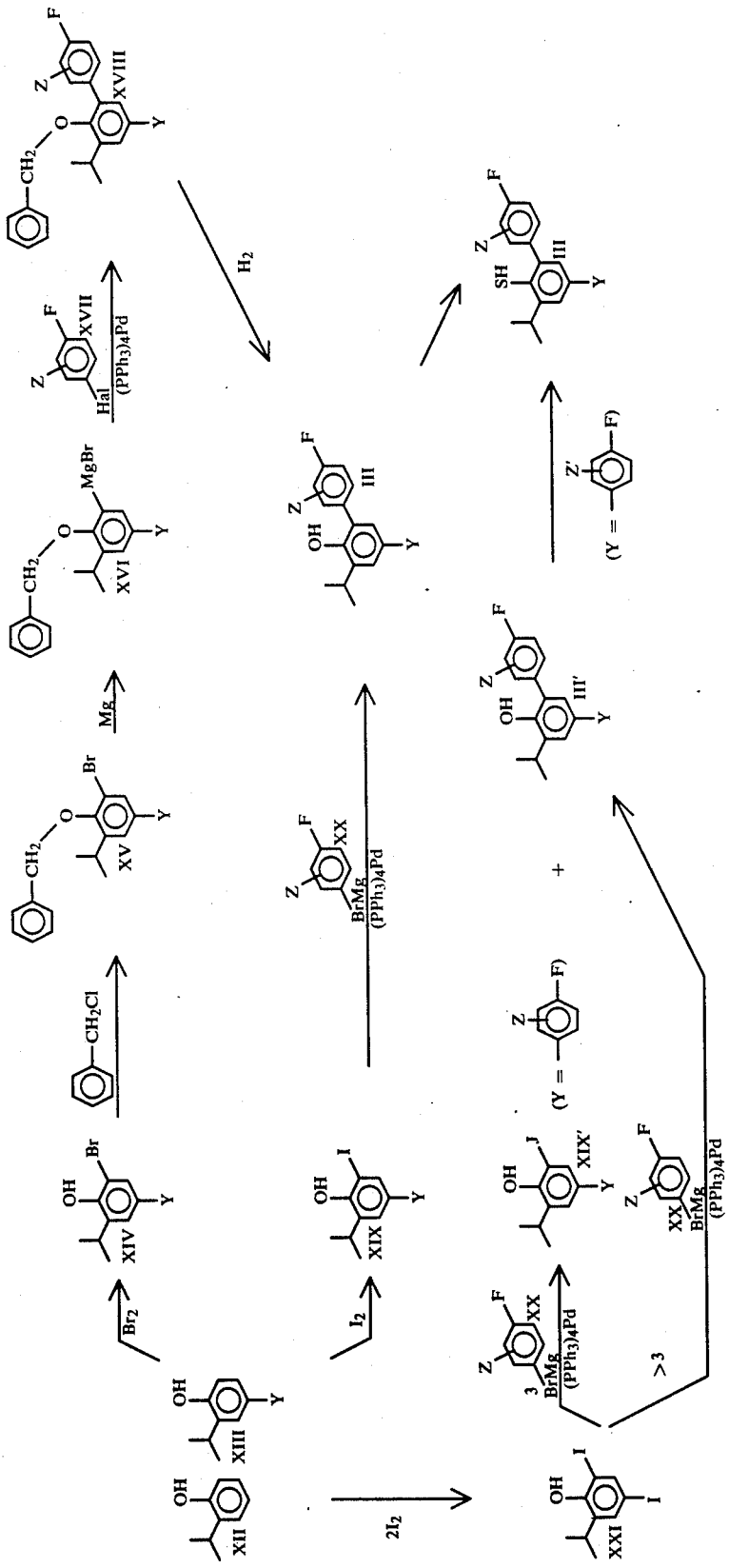

Synthesis routes for the preparation of compounds of the formula XIII (reaction scheme 1) are outlined in part in reaction scheme 2 and described below.

The preparation of the starting compound XIII with certain substituents Y depends on the availability of starting materials.

XIII (Y=i-Pr) is formed by decarboxylation of commercially obtainable 3,5-diisopropyl-2-hydroxybenzoic acid of the formula XI (Janssen). The decarboxylation can be carried out by heating the pure substance or a solution in an inert solvent (for example nitrobenzene) to 210° to 220° C. A considerably better yield and purity is obtained if a solution in quinoline is heated at about 190° C. in the presence of a copper chromite catalyst.

XIII (Y=tert.-butyl) is obtained highly para-selectively according to G. Sartori et al., Chem. and Industry, 762 (1985) if isopropylphenol is stirred in $CH_2Cl_2$ solution with methyl tert.-butyl ether (MTBE) and zirconium(IV) chloride. A good yield of XIII is obtained if XII (1.0 equivalent) is reacted with MTBE (1.05 equivalents) and $ZrCl_4$ (2.4 equivalents in 2 portions) at 0° C.

Conventional Friedel-Crafts alkylations of XII with corresponding alkyl halides/aluminum trichloride or with alcohols Y-OH/Lewis or proton acids can also be used for the preparation of XIII [see K.-D. Bode in Houben-Weyl "Methoden der organischen Chemie (Methods of Organic Chemistry)" Volume VI/1c "Phenole Teil 2 (Phenols Part 2)", Georg Thieme Verlag, Stuttgart (1976), page 925 et seq.].

4-Hydroxy-3-isopropyl-biphenyl XIII

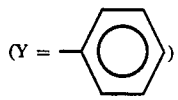

is obtained from commercially available p-nitrobiphenyl VIII by o-alkylation with isopropylmagnesium bromide [Review by G. Bartoli, Acc. Chem. Res. 17, 109 (1984)] to give IX, reduction of IX to the amine X, diazotization and decomposition to the phenol by boiling (reaction scheme 2).

Catalytic hydrogenation of an ethyl acetate solution of XIII

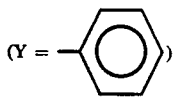

over 5% palladium-on-charcoal at 50° C. under a hydrogen pressure of 4 to 6 kg cm$^{-2}$ gives XIII

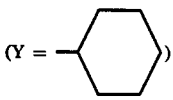

in a yield of 85 to 90%:

Reaction scheme 2

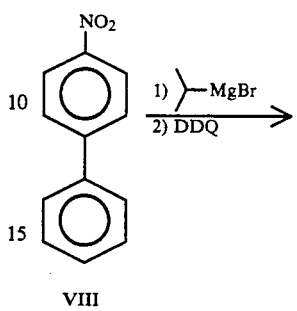

VIII

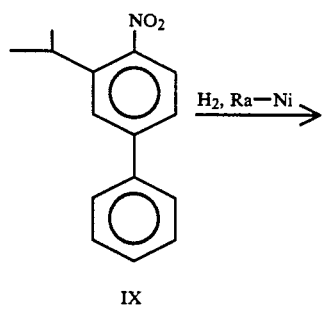

IX

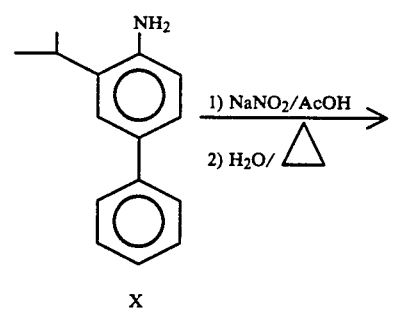

X

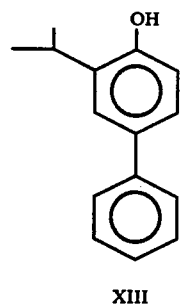

XIII

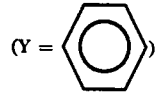

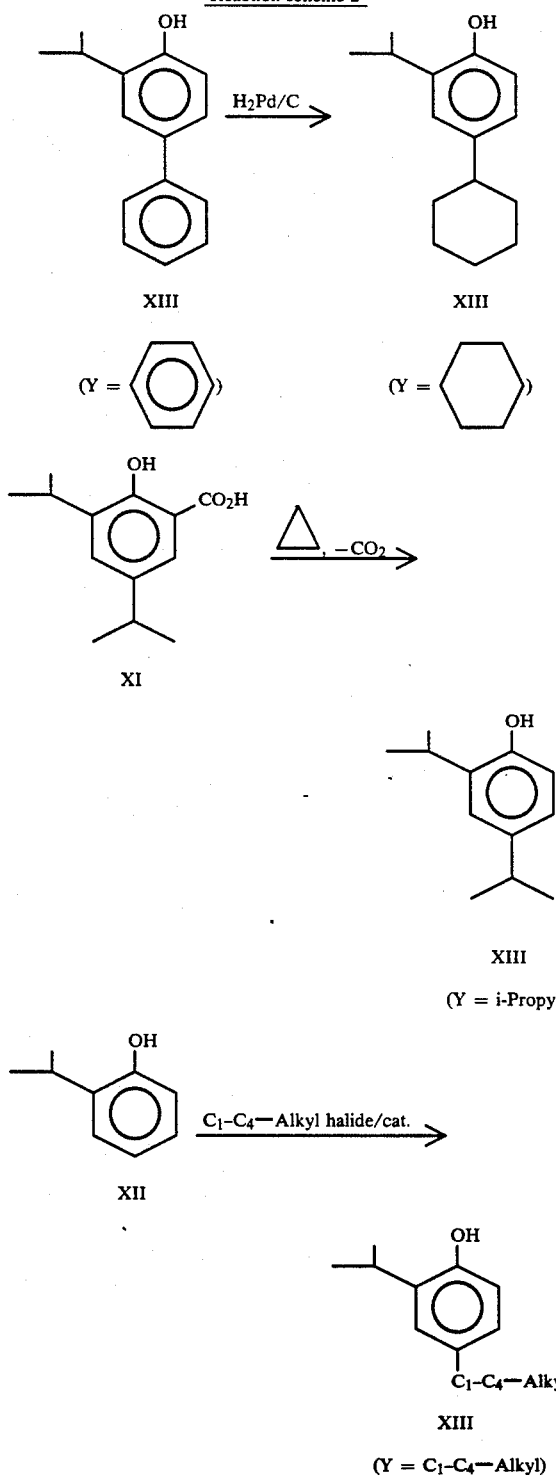

-continued
Reaction scheme 2

The lactones of the formula I can be converted into the corresponding open-chain dihydroxycarboxylic acids of the formula II, pharmacologically tolerated salts thereof with bases and pharmacologically tolerated esters thereof by a customary method (cf. for example EP-A-0,216,127 and DE-A-3,632,893).

The enzyme HMG-CoA reductase is widespread in nature. It catalyzes the formation of mevalonic acid from HMG-CoA. This reaction is a central step in cholesterol biosynthesis (I.R. Sabine, 3-Hydroxy-3-methylglutaryl coenzyme A reductase, CRC Press, 1983). High cholesterol levels are associated with a number of diseases, such as, for example coronary heart disease or atherosclerosis. The reduction of increased cholesterol levels for prevention and treatment of such diseases is therefore a therapeutic aim. One point of attack lies in inhibition or reduction of endogenous cholesterol synthesis. Inhibitors of HMG-CoA reductase block cholesterol biosynthesis at an early stage. They are therefore suitable for the prevention and treatment of diseases caused by an increased cholesterol level. A reduction or decrease in endogenous synthesis leads to an increased uptake of cholesterol from plasma in the cells. An additional effect can be achieved by simultaneous administration of substances which bind bile acids, such as anion exchangers. The increased secretion of bile acids leads to an increased renewed synthesis and therefore to an increased cholesterol breakdown (M.S. Brown, P.T. Kovanen, J.L. Goldstein, Science 212, 628 (1981): M.S. Brown, J.L. Goldstein Spektrum der Wissenschaft 1985 (1), 96). The compounds according to the invention are inhibitors of HMG-CoA reductase. They are therefore suitable for inhibition or reduction of cholesterol biosynthesis and hence for prevention or treatment of diseases caused by an increased cholesterol level, in particular coronary heart disease, atherosclerosis, hypercholesterolemia, hyperlipoproteinemia and similar diseases.

The invention therefore also relates to pharmaceutical preparations based on compounds of the formula I or the corresponding dihydroxycarboxylic acids of the formula II or salts and esters thereof and the use of these compounds as pharmaceuticals, in particular for the treatment of hypercholesterolemia.

The compounds of the formula I and the corresponding acids, salts or esters are administered in various dosage forms, preferably orally in the form of tablets, capsules or liquids. The daily dose varies in the range from 3 mg to 2,500 mg, but preferably in the dose range from 10 to 500 mg, depending on the body weight and constitution of the patient.

The compounds according to the invention can be used as lactones of the general formula I, in the form of the free acids of the formula II or in the form of pharmaceutically acceptable salts or esters, and in particular as a solution or suspension in pharmacologically acceptable organic solvents, such as mono- or polyhydric alcohols, such as, for example, ethanol or glycerol, in triacetin, oils, such as, for example, sunflower oil or cod-liver oil, ethers, such as, for example, diethylene glycol dimethyl ether or polyethers, such as, for example, polyethylene glycol, or in the presence of other pharmacologically acceptable polymeric carriers, such as, for example, polyvinylpyrrolidone, or other pharmaceutically acceptable additives, such as starch, cyclodextrin or polysaccharides. The compounds according to the invention can furthermore be combined with additives which bind bile acids, in particular non-toxic basic anion exchanger resins which bind bile acids in a nonresorbable form in the gastrointestinal tract. The salts of the dihydroxycarboxylic acids can also be processed as an aqueous solution.

The HMG-CoA reductase activity of the sodium salts of the compounds of the formula II according to the invention has been determined in two test systems Inhibition of the HMG-CoA Reductase Activity on Solubilized Enzyme Preparations from Rat Liver Microsomes The HMG-CoA. reductase activity was measured on solubilized enzyme preparations from liver microsomes from rats, which were induced with cholestyramine (®Cuemid) after changing into the day/night rhythm. (S,R) $^{14}$C-HMG-CoA was used as the substrate and the concentration of NADPH was maintained during the incubation by means of a regenerating system. $^{14}$C-Mevalonate was separated off from the substrate and other products (for example $^{14}$C-HMG) via column elution, the elution profile of each individual sample being determined. Continuous simultaneous treatment of $^3$H-mevalonate was dispensed with, since the determination relates to relative information on the inhibiting action. In each case the enzyme-free control, the enzyme-containing normal batch (=100%) and batches containing additions of preparation were treated together in one test series. Each individual value was obtained as a mean value from 3 parallel samples. The significance of the differences between the mean values of the preparation-free and preparation-containing samples were evaluated by the t-test. In the method described above, the following inhibiting values on HMG-CoA reductase were determined, for example, for the compounds according to the invention (IC$_{50}$ (mole/1); molar concentration of the compound per liter required for a 50% inhibition)

TABLE 1

| Example | IC$_{50}$ (mole/l) |
|---|---|
| 8a | $2.3 \cdot 10^{-9}$ |
| 8b | $>10^{-7}$ |
| 8c | $1.7 \cdot 10^{-8}$ |
| 8d | $2.3 \cdot 10^{-8}$ |
| 8e | $5.2 \cdot 10^{-9}$ |
| 8f | $4.8 \cdot 10^{-9}$ |
| 8g | $3.6 \cdot 10^{-8}$ |

Suppression or inhibition of HMG-CoA Reductase in HEP G2 Cell Cultures (of a Human Hepatoma Cell Line)

The inhibition of the incorporation of $^{14}$C-sodium acetate into cholesterol was determined.

Monolayers of HEP G2 cells in RPMJ 1640 medium with 10% of fetal calf serum freed from lipids were preincubated with various concentrations of the sodium salts of the dihydroxycarboxylic acids of the formula II for 1 hour. After addition of $^{14}$C-labeled sodium acetate, the incubation was continued for 3 hours. Tritium-labeled cholesterol was added as an internal standard and an aliquot of the cells was subjected to alkaline hydrolysis. The lipids were extracted with chloroform-/methanol 2:1. After addition of carrier cholesterol, the lipid mixture was separated preparatively on thin-layer chromatography plates with chloroform/acetone 9:1. The cholesterol zone was rendered visible by staining with iodine vapor and was also detected with a thin layer chromatography radioscanner and then scraped off. The amount of $^{14}$C-cholesterol was determined by scintigraphy. In another aliquot of the cell monolayer, the cell protein was measured (for calculation of the $^{14}$C-cholesterol biosynthesis per mg of cell protein). The same procedure was performed with cells of the same culture without preincubation with a test compound (so-called "solvent control"). The potency of the test compounds was determined by comparison of the biosynthesized $^{14}$C-cholesterol in the test runs and in the "solvent control". The potency was calculated on the basis of mevinolin sodium salt as an external standard. The IC$_{50}$ and IC$_{70}$ values (IC$_{50}$ or IC$_{70}$ (M) is the molar concentration of the compound per liter required for 50 or 70% inhibition respectively) varied somewhat for different cell batches. The mean values for mevinolin sodium salt were IC$_{50}$=5×10$^{-8}$M, IC$_{70}$=1.5×10$^{-7}$M. The IC's measured for test compounds (sodium salts of the dihydroxycarboxylic acids of the formula II) (Table 2) were corrected by the deviation of mevinolin sodium from its average value. Mevinolin sodium was attributed a relative potency of 100.

TABLE 2

| Example | IC$_{50}$ (M) | IC$_{70}$ (M) | relative potency |
|---|---|---|---|
| 8a | $2.7 \cdot 10^{-8}$ | $7 \cdot 10^{-8}$ | 185 (214) |
| 8b | $\sim 10^{-5}$ | | <1 |
| 8c | $9 \cdot 10^{-8}$ | | 56 |
| 8d | $9.5 \cdot 10^{-8}$ | | 53 |

The synthesis of the compounds I according to the invention is to be illustrated further. by the following examples.

EXAMPLE 1

Synthesis of 4(R)-hydroxy-6(S)-[(2,4-diisopropyl-6-p-fluorophenyl)-phenoxymethyl]tetrahydro-2H-pyran-2-one (Formula I, X=O, Y=i-Pr, Z=H)

EXAMPLE 1.1

2,4-Diisopropylphenol (Formula XIII, Y=i-Pr)

A mixture of 145 g (0.65 mole) of 3,5-diisopropyl-2-hydroxybenzoic acid (XI), 540 ml (588 g, 4.55 mole) of quinoline and 7.5 g (0.024 mole) of copper chromite (2CuO.Cr$_2$O$_3$) is stirred at 190° C. (225° C. external temperature) for 2 hours. The mixture is cooled to about 10° C., acidified to pH 1 to 2 with about 1 l of half-concentrated hydrochloric acid, while cooling further, and extracted with toluene and the extract is washed with 2N hydrochloric acid, then with water and subsequently with NaHCO$_3$ solution. It is dried, filtered and concentrated and the residue is distilled under a high vacuum. 105 g of the title compound XIII are obtained as a pale yellow , oil, boiling point 81° to 84° C./0.2 mm Hg.

$^1$H-NMR(CDCl$_3$): δ 1.20 (6H,d); 1.25 (6H,d); 3.00 (2H,2x hept ); 4.10 (1H,s,br); 6.50–7.00 (3H,m)

EXAMPLE 1.2

2,4-Diisopropyl-6-bromophenol (Formula XIV, Y=i-Pr) 1 g of iron powder is added to a hot solution, at 95° C., of 102.3 g (0.57 mole) of 2,4-diisopropylphenol in 900 ml of glacial acetic acid, and 101g (32.2 ml, 0.63 mole) of bromine are then added dropwise in the course of 90 minutes. The reaction mixture is stirred at 100° C for a further hour and partitioned between toluene and water and the toluene phase is washed with NaHCO$_3$ solution. It is dried, filtered and concentrated and the residue is distilled under a high vacuum. 125 g of the title compound XIV are obtained as a pale yellow oil, boiling point 85° C./0.15 mm Hg.

$^1$H-NMR(CDCl$_3$): δ 1.20 (6H,d); 1.25 (6H,d); 2.80 (1H, hept.); 3.25 (1H,hept.); 5.33 (1H,s); 6.87–7.20 (2H,m)

MS (70 eV): m/e=256/258 (M+), 241/243 (M+-CH$_3$)

EXAMPLE 1.3

1-Benzyloxy-2,4-diisopropyl-6-bromobenzene (Formula XV, Y=i-Pr)

A suspension of 166.5 g (1.2 mole) of potassium carbonate in 124 g (0.48 mole) of the above bromophenol, 91.52 g (0.72 mole) of benzyl chloride and 2 l of 2-butanone is heated under reflux for 24 hours. The suspension is cooled, the inorganic solid is filtered off with suction, the filtrate is concentrated in vacuo and the residue is partitioned between toluene and water. The toluene phase is washed with saturated sodium chloride solution, dried, filtered and concentrated. The residue is chromatographed with cyclohexane/toluene 9:1 over silica gel. 155 g of the title compound XV are obtained as a colorless oil. Small residual amounts of benzyl chloride are removed under a high vacuum. The purification can also be achieved by distillation (boiling point 150° C./0.15 mm Hg).

$^1$H-NMR(CDCl$_3$): δ 1.18 (6H,d); 1.22 (6H,d), 2.80 (1H, hept.); 3.32 (1H,hept.); 4.90 (2H,s); 6.93–7.60 (7H,m)

MS (70 eV): m/e=346/348 (M+), 267, 254/256, 91

EXAMPLE 1.4

1-Benzyloxy-2,4-diisopropyl-6-p-fluorophenylbenzene (Formula XVIII, Y=i-Pr, Z=H)

The Grignard compound X (Y=i-Pr) is prepared from 48.62 g (0.24 mole) of the bromide from Example 1.3 and 3.53 g (0.147 mole) of Mg filings in 120 ml of absolute tetrahydrofuran (~60° C., 1 hour). This Grignard solution is added rapidly to a solution of 31.08 g (0.14 mole) of 4-fluoroiodobenzene and 3.23 g (2.8 mmol) of tetrakis(trihenylphosphine)palladium(O) in 140 ml of absolute tetrahydrofuran. The internal temperature rises to 55° to 60° C. within 15 minutes. After 7 minutes, a precipitate forms. The mixture is stirred at 50° to 58° C. for 1 hour, left to stand overnight at room temperature and partitioned between ether and 1 N hydrochloric acid and the ether phase is washed with 1 N hydrochloric acid, then with water and subsequently with saturated NaHCO$_3$ solution. It is dried, filtered and concentrated. If required, the product is purified by chromatography with cyclohexane/toluene 4:1 over silica gel or by distillation (boiling point 180° C./0.3 mm Hg). 49.3 g of the title compound XVIII are obtained as a colorless solid, melting point 65° to 67° C.

$^1$H-NMR(CDCl$_3$): δ 1.30 (12H,d); 2.95 (1H,hept.); 3.45 (1H, hept.); 4.40 (2H,s); 6.90–7.80 (11H,m)

MS (CI): m/e=363 (M+H+), 362 (M+), 285, 263

EXAMPLE 1.5

2,4-Diisopropyl-6-p-fluorophenylphenol (Formula III, Y=i-Pr, Z=H)

4 g of 10% Pd-on-charcoal are added to a solution of 49.3 g (0.136 mole) of the benzyl ether XVIII from Example 1.4 in 1 l of ethyl acetate and 100 ml of glacial acetic acid and the mixture is shaken in a hydrogen atmosphere for 20 minutes (vigorous uptake of H$_2$). The catalyst is filtered off, the filtrate is concentrated and the residue is taken up several times in toluene and concentrated in vacuo each time. 34.4 g of the title compound III are obtained as a colorless oil, boiling point 115° C./0.1 mm Hg.

$^1$H-NMR(CDCl$_3$, 270MHz): δ 1.25 (6H,d); 1.29 (6H,d); 2.87 (1H, hept.); 3.31 (1H,hept.); 4.95 (1H, s,br); 6.88 (1H,d); 7.08 (1H,d) 7.18 (2H,m); 7.45 (2H,m).

MS (70 eV): m/e=272 (M+), 257 (M+-CH$_3$)

EXAMPLE 1.6

6(S)-{(2,4-Diisopropyl-6-p-fluorophenyl)phenoxymethyl}-3,4,5,6-tetrahydro-2(R,S)-methoxy-4(R)-(t-butyldiphenylsilyloxy)-2H-pyran (Formula V, Y=i-Pr, Z=H)

27.2 g (0.1 mole) of the phenol from Example 1.5 are added to a suspension of 27.6 g (0.2 mole) of potassium carbonate and a spatula-tip of hydroquinone in 250 ml of absolute dimethyl sulfoxide. The mixture is stirred at room temperature for 1 hour and a solution of 56 g (0.11 mole) of the lactol ether iodide IV (for the preparation see EP-A 0,216,127, R$_7$=t-butyldiphenylsilyl) in 250 ml of absolute dimethyl sulfoxide is then added. The mixture is stirred at an internal temperature of 50°–55° C. for 4 hours. Thin-layer chromatography (silica gel, 1st development with cyclohexane/ethyl acetate 9:1, 2nd development with cyclohexane/ethyl acetate 15:1) indicates complete conversion of the iodide IV (R$_f$0.5), a little residual starting phenol (R$_f$0.7) and mainly product of the formula V (R$_f$0.6). The reaction mixture is allowed to cool and is partitioned between ether and half-saturated sodium chloride solution. The aqueous phase is extracted again with ether. The combined organic phases are washed with sodium chloride solution, dried over MgSO$_4$, filtered and concentrated. The crude product is chromatographed with toluene/cyclohexane 2:1, then 100% toluene and then toluene/ethyl acetate 30:1 over silica gel. 51 g of the title compound are obtained as a colorless resin.

$^1$H-NMR(CDCl$_3$): δ 1.10 (9H,s); 1.28 (12H,d), 1.4–2.2 (4H,m); 2.93 (2H,2xhept.); 3.40 (2H,m); 3.52 (3H,s); 3.97–4.40 (2H,qui+m); 4.87 (1H,dd); 6.87–7.90 (16H,m)

MS (CI): m/e=654 (M$^{30}$), 597 (M$^{30}$-tert.-bu), 539, 519, 323, 283, 135, 127

EXAMPLE 1.7

6(S)-(2,4-Diisopropyl-6-p-fluorophenyl)phenoxymethyl}-3,4,5,6-tetrahydro-2-(R,S)-hydroxy-4(R)-(t-butyldiphenylsilyloxy)-2H-pyran (Formula vI, Y=i-Pr, Z=H)

A solution of 40.2 g (61.4 mmol) of the lactol ether from Example 1.6 in 3 l of tetrahydrofuran, 3 l of water and 4.2 l of glacial acetic acid is stirred at 80°–85° C. (external temperature) for 24 hours. The solvents are removed in vacuo and the residue is evaporated with fuming 3 times with toluene in vacuo. Chromatography with cyclohexane/ethyl acetate 12:1 through 2 l of silica gel gives 33.4 g (yield of 85%) of the title compound as a . colorless amorphous powder.

MS (FAB): m/e=640 (M+), 519, 367, 323, 283, 271, 257

EXAMPLE 1.8

6(S)-{2,4-Diisopropyl-6-p-fluorophenyl)phenoxymethyl}-3,4,5,6-tetrahydro-4(R)-(t-butyldiphenylsilyloxy)-2H-pyran-2-one (Formula VII, Y=i-Pr, Z=H)

46.9 g (208.4 mmol) of N-iodosuccinimide are added to a solution of 33.4 g (52.1.mmol) of the lactol from Example 1.7 and 19.25 g (52.1 mmol) of tetrabutylammonium iodide in 2.5 l of absolute methylene chloride, while stirring and cooling. The mixture is stirred under nitrogen with exclusion of light at 10° C. for 1 hour and at room temperature for 20 hours. The reaction solution is washed with water, then twice with NaHSO$_3$ solution and subsequently with saturated NaCl solution, dried, filtered and concentrated. The residue is dissolved in a little methylene chloride and filtered through silica gel with cyclohexane/ethyl acetate 92:8. 32.1 g of the title compound are obtained as a colorless resin.

$^1$H-NMR(CDCl$_3$, 270MHz): δ 1.06 (9H,s); 1.23 (6H,d); 1.26 (6H,d); 1.59 (2H,m); 2.41 (1H, dd); 2.59 (1H,dm); 2.90 (1H, hept.); 3.36 (1H,hept.); 3.48 (2H, AB of ABX); 4.29 (1H,qui); 4.80 (1H,m); 6.96 (1H,d); 7.03 (2H,m); 7.10 (1H,d); 7.36–7.52 (8H,m); 7.58–7.73 (4H,m)

MS (70 eV, 70° C.): m/e=638 (M+), 581 (M+-tert.-bu), 539 (581 - propene), 283, 199

EXAMPLE 1.9

4(R)-Hydroxy-6(S)-[(2,4-diisopropyl-6-p-fluorophenyl)phenoxymethyl]tetrahydro-2H-pyran-2-one (Formula I, X=O, Y=i-Pr, Z=H)

11.65 g (194 mmol) of glacial acetic acid, followed by 45.92 g (145.5 mmol) of tetrabutylammonium fluoride trihydrate, are added to a solution of 31.0 g (48.5 mmol) of the silyl compound from example 1.8 in 1.5 l of tetrahydrofuran (filtered over basic Al$_2$O$_3$). The mixture is stirred at room temperature for 20 hours. The solvents are removed in vacuo and the residue is immediately partitioned between ether and water. The aqueous phase is extracted twice more with ether. The combined organic phases are washed with saturated sodium chloride solution, dried over MgSO$_4$, filtered and concentrated. The residue is taken up in toluene and the mixture is concentrated in vacuo. The crude product is chromatographed with cyclohexane/ethyl acetate 1:1 through 2 kg of silica gel. 15.7 g (yield of 81%) of the title compound are obtained as a colorless solid, melting point 145°–147° C.

$^1$H-NMR(CDCl$_3$, 270MHz): δ 1.25 and 1.27 (12H,2xd); 1.67 (1H,s,br.); 1.76 (1H,dtd); 1.87 (1H,ddd); 2.58 (1H,ddd); 2.69 (1H,dd); 2.91 (1H,hept); 3.39 (1H,hept), 3.54 (2H,AB of ABX); 4.38 (1H,qui), 4.68 (1H,m); 6.97 (1H,d); 7.10 (3H,d+m); 7.51 (2H,m)

MS (FAB): m/e=400 (M+), 257

EXAMPLE 2

Synthesis of
4(R)-hydroxy-
-6(S)-[(2-isopropyl-4-tert.-butyl-6-p-fluorophenyl)-phenoxymethyl]tetrahydro-2H-pyran-2-one (Formula I, X=O, Y=tert.-bu, Z=H)

EXAMPLE 2.1

2-Isopropyl-4-tert.-butylphenol (Formula XIII, Y=tert.-bu)

A solution of 34 g (0.25 mole) of o-isopropylphenol (formula XII) and 22 g (0.26 mole) of tert.-butyl methyl ether in 150 ml of absolute CH$_2$Cl$_2$ is slowly added dropwise to a suspension of 70 g (0.3 mole) of zirconium tetrachloride in 100 ml of absolute CH$_2$Cl$_2$ at −5° to 0° C. under nitrogen. The mixture is stirred at 0° C. for 1 hour. Thin-layer chromatography (100% toluene) indicates a conversion of about 50%. A further 70 g (0.3 mole) of ZrCl$_4$ are rapidly added all at once and the brown suspension is stirred at 0° C. for 15 minutes. Thin-layer chromatography now indicates a conversion of >95% and no impurities at all.* 500 ml of saturated NaHCO$_3$ solution are slowly added dropwise at −10° to 0° C., under very good cooling (very exothermic). A colorless solid which makes mechanical stirring very difficult forms. The organic phase is separated off, dried and concentrated in vacuo. If required, the product is chromatographed with cyclohexane/toluene 1:2 through 800 g of silica gel or is distilled in vacuo. 43.1 g of the title compound XIII are obtained as a colorless solid, melting point 55° to 57° C., boiling point 134° to 135° C./12 mm Hg.

$^1$H-NMR(CDCl$_3$): δ 1.27 (6H,d); 1.28 (9H,s); 3.17 (1H, hept.); 4.61 (1H,s); 6.62 (1H,d); 7.05 (1H,dd); 7.17 (1H,d)

MS (70 eV): m/e=192 (M$_+$)

* If the mixture is left to stand at room temperature under nitrogen for 10 hours, thin-layer chromatography again indicates about 30% of starting material and numerous by-products.

EXAMPLE 2.2

2-Isopropyl-4-tert.-butyl-6-bromophenol (Formula XIV, Y=tert.-bu)

18 ml (55.8 g, 0.35 mole) of bromine are added dropwise to a solution of 65.8 g (0.34 mole) of the phenol XIII from Example 2.1 in 375 ml of CCl$_4$. Complete conversion of the starting material is checked by thin-layer chromatography (cyclohexane/ethyl acetate 5:1, R$_f$ XIII: 0.37, XIV: 0.33), the product is taken up in ether and the solution is washed twice with Na$_2$S$_2$O$_3$ solution and once with saturated NaCl solution. It is dried, concentrated and distilled under a high vacuum. 86.1 g of the title compound XIV are obtained as a pale yellow oil, boiling point 105° to 106° C./1 mm Hg.

$^1$H-NMR(CDCl$_3$): δ 1.25 (6H,d); 1.29 (9,s); 3.47 (1H, hept.); 6.17 (1H,br.); 7.09 (1H,d); 7.24 (1H,d)

MS (70 eV): m/e=270/272 (M+)

EXAMPLE 2.3

2-Isopropyl-4-tert.-butyl-6-iodophenol (Formula XIX, Y=tert.-bu)

A solution of 30.4 g (0.12 mole) of iodine and 40.0 g (0.24 mole) of potassium iodide in 120 ml of water is added dropwise to a solution of 19.2 g (0.1 mole) of the phenol XIII from Example 2.1 in 150 ml of 50% strength aqueous ethylamine solution and 120 ml of ethanol at 20° to 25° C. The mixture is stirred at room temperature for 1 hour, the product is taken up in ether, the ether extract is washed twice with Na$_2$S$_2$O$_3$ solution and then with saturated NaCl solution, dried and concentrated in vacuo, the residue is taken up in toluene and the solution is concentrated in vacuo at <25° C. 26.0 g of the title compound XIX are obtained as an oil.

$^1$H-NMR(CDCl$_3$): δ 1.15–1.50 (15H,s+d); 3.06 (1H,hept.); 4.60 (1H,s,br.); 6.86 (1H,s); 7.73 (1H,s)

MS (70 eV, <50° C.): m/e=318 (M+), 303 (M+-CH$_3$), 275, 177, 161

EXAMPLE 2.4

1-Benzyloxy-2-isopropyl-4-tert.-butyl-6-bromobenzene
(Formula XV, Y=tert.-bu)

is obtained analogously to Example 1.3 from the compound XIV, Example 2.2. Colorless crystals, melting point 47° to 49° C.

$^1$H-NMR(CDCl$_3$): δ1.23 (6H,d); 1.48 (9H,s); 3.33 (1H, hept.); 5.12 (2H,s); 7.02 (1H,s); 7.44 (6H,s,br.)

MS (70 eV): m/e=360/362 (M+), 268/270, 91

EXAMPLE 2.5

1-Benzyloxy-2-isopropyl-4-tert.-butyl-6-p-fluorophenylbenzene (Formula XVIII, Y=tert.-bu, Z=H)

is obtained analogously to Example 1.4 from the corresponding Grignard compound XVI. Colorless solid, melting point 126° to 128° C.

$^1$H-NMR(CDCl$_3$): δ 1.1–1.3 (15H,s+d); 3.38 (1H,hept.); 5.16 (2H,s); 6.83 (1H,s); 7.0–7.7 (10H,m)
MS (70 eV): m/e=376 (M$^+$), 282, 91

EXAMPLE 2.6

2-Isopropyl-4-tert.-butyl-6-p-fluorophenylphenol (Formula III, Y=tert.-bu, Z=H)

is obtained analogously to Example 1.5 from the compound XVIII from Example 2.5. Colorless solid, melting point 109° to 111° C.

$^1$H-NMR(CDCl$_3$): δ 1.15 (9H,s); 1.23 (6H,d); 3.16 (1H, hept.); 4.65 (1H,s); 6.80 (1H,s); 6.9–7.4 (5H,m)
MS (70 eV): m/e=286 (M$^+$), 271 (M$^+$-$CH_3$), 229

EXAMPLE 2.7

2-Isopropyl-4-tert.-butyl-6-p-fluorophenylphenol (Formula III, Y=tert.-bu, Z=H) by direct coupling of the iodide XIX with the Grignard reagent from p-bromofluorobenzene XX 1./87 g (1.6 mmol) of tetrakis(triphenylphosphine)-palladium (O) are added to a solution of 25.7 g (81 mmol) of the iodophenol from Example 2.3 in 150 ml of absolute tetrahydrofuran and the mixture is stirred at room temperature for 30 minutes. The Grignard reagent obtained from 42.6 g (243 mmol) of 4-bromofluorobenzene and 6.2 g (255 mmol) of Mg filings in 170 ml of tetrahydrofuran is added all at once. During this addition, the internal temperature rises to about 50° C. The mixture is kept at 55° C. for 3 hours, during which a colorless solid (magnesium iodide) separates out.* The reaction mixture is taken up in ether and the ether extract is washed twice with 1N hydrochloric acid, once with water and once with saturated sodium bicarbonate solution, dried and concentrated in vacuo. The residue is chromatographed with cyclohexane/ethyl acetate 9:1 over 1 kg of silica gel. The fractions containing XIII, XIX and III are concentrated together. The residue is dissolved in the minimum amount of n-pentane. 9.8 g of pure III crystallize in a deep-freeze. The melting point and spectrum of this material were identical to those given in Example 2.6.

* The course of the reaction cannot be monitored by thin-layer chromatography since the iodide XIX, the coupling product III and the phenol XIII, which is formed as a by-product during coupling, cochromatograph in all the usual mobile phases. Suitable separating conditions: high performance liquid chromatography on a 250x4.6 RP column of 18.5 μm Nucleosil, 64% (CH$_3$OH+0.1% NH$_4$OAc)/36% H$_2$O, 1.2 ml/minute, 40° C., UV detection at 254 nm.

EXAMPLES 2.8 to 2.11

4(R)-Hydroxy-6(S)-[2-isopropyl-4--tert.-butyl-6-p-fluorophenyl)phenoxymethyl]tetrahydro-2H-pyran-2-one (Formula I, X=0, Y=-tert.-bu, Z=H)

is obtained from the phenol III (Example 2.6 or 2.7) analogously to Examples 1.6 to 1.9. Colorless solid, melting point 178°–179° C.

$^1$H-NMR(CD$_2$CD$_2$): δ 1.13–1.20 (15H,m), 2.02 (1H,s,br.), 2.10–2.16 (2H,m), 2.71 (2H,AB of ABX), 3.24 (1H,hept.), 4.22 (2H,AB of ABX), 4.0 (1H,s,br.), 5.03–5.13 (1H,m), 6.79 (1H,s), 6.98–7.07 (3H,m), 7.19–7.25 (2H,m)

MS (70 eV): m/e=414 (M$^+$), 359 IR (KBr): 3560/3460 (OH), 1745, (C=O), 1500, 1235, 1220 cm$^{-1}$

EXAMPLE 3

Synthesis of 4(R)-hydroxy-6(S)-[(2-isopropyl-4,6-di-pfluorophenyl)-phenoxymethyl]tetrahydro-2H-pyran-2-one

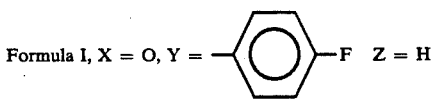

Formula I, X = O, Y = —⟨○⟩—F   Z = H

EXAMPLE 3.1

2-Isopropyl-4,6-diiodophenol (Formula XXI)

A solution of 160 g (0.63 mole) of iodine and 209 g (1.26 mole) of potassium iodide in 300 ml of water is added dropwise to a solution of 40.8 g (0.3 mole) of oisopropylphenol in 630 ml of 50% strength aqueous ethylamine solution and 525 ml of ethanol at 0°–15° C. in the course of 10 minutes. The reaction mixture is stirred at room temperature for 20 minutes and poured onto 200 ml of saturated Na$_2$S$_2$O$_3$ solution plus 600 ml of water. The mixture is extracted with 3×500 ml of ether and the combined extracts are washed with E./2 N hydrochloric acid and then with water. They are dried over MgSO$_4$ and decanted onto fresh MgSO$_4$, the mixture is filtered and the filtrate is concentrated in vacuo at <20° C. 100 ml of toluene are added and the mixture is concentrated in vacuo at <20° C. This operation of evaporation by fuming with toluene is repeated once under a waterpump vacuum and once under a high vacuum. 99.0 g of the title compound are obtained as a red oil. No impurities are detectable by NMR, MS or thin-layer chromatography.

$^1$H-NMR(CDCl$_3$): δ 1.2 (6H,d), 3.2 (1H,hept.), 3.5 (1H,s), 7.35 (1H,d), 7.75 (1H,d)
MS (70 eV): m/e 388 (M$^+$), 373 (M$^+$-CH$_3$), 246 (M$^+$-CH$_3$I)

EXAMPLE 3.2

2-Isopropyl-4,6-di-p-fluorophenylphenol (Formula III', Z=H)

The Grignard solution obtained from 219 g (1.25 mole of p-bromofluorobenzene and 31.3 g (1.3 mole) of magnesium filings in 600 ml of absolute tetrahydrofuran is added dropwise to a solution of 125 g (0.32 mole) of the diiodide XXI from Example 3.1 and 5 g (7.1 mmol) of bis(triphenylphosphine)palladium(II) chloride (Aldrich) in 300 ml of absolute tetrahydrofuran under argon and while cooling with ice (internal temperature of 25°–30° C). The mixture is stirred at 40°–50° C. for 5 hours, a further 2.5 g of (PPh$_3$)$_2$PdCl$_2$ are then added and the mixture is stirred overnight at about 45° C. It is cooled to 0° C. and 50 ml of water are added dropwise (exothermic reaction) at such a rate that the internal temperature remains below 25° C. A viscous slimy precipitate forms 300 ml of half-concentrated hydrochloric acid are added dropwise at 25° C. (precipitate dissolves, pH~1). The mixture is extracted several times with ether. The combined extracts are washed with 1N hydrochloric acid, then with saturated NaHCO$_3$ solution and subsequently with saturated sodium chloride solution and then dried and concentrated. A black viscous oil is obtained which is chromatographed through 1 kg of silica gel 70-200 μm, first with 4 l of cyclohexane/toluene (4:1), then with 10 l of cyclohexane/toluene (3:1) and subsequently with cyclohexane/toluene (2.5:1).

10.2 g of a colorless solid which, according to NMR (only aromatic protons) MS: 360, 342, 284, 266 (base peak), 248 and analysis (C+H+F 100%), is an oligomer mixture formed from the Grignard compound XX (Z=H) are first eluted.
m/e=266 coresponds to

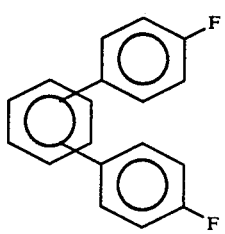

248 is 266-F+H, 284 is 266+F-H, 360 is 266+CsH F-H, 342 is 360-F+H. 2.1 9 of a mono-couplin9 product which is 2-isopropyl-4-p-fluorophenyl-6-iodophenol XIX, (Y =p-fluorophenyl) are then eluted.

MS (70 eV): m/e=356 (M+), 341 (M$^{30}$ -CH:), 214

Finally, 45.1 g of the title compound III, are eluted as a viscous colorless oil which crystallizs on prolonged standing at room temperature.

$^1$H-NMR(CDCl$_3$): δ 1.35 (6H,d); 3.4 (1H,hept.); 5.1 (1H,s); 6 8-7.6 (10H,m)

MS (70 eV): m/e=324 (M+), 309 (M$^{30}$ -CH$_3$) Thin-layer chromatography (toluene/cyclohexane 1:2) R$_f$ values: oligomer mixture 0.61, starting material XXI 0.53, monoiodide XIX, 0.50, product III': 0.35

EXAMPLES 3.3 to 3.6

4(R)-Hydroxy-6(S)-[(2-isopropyl-4,6-di-p-fluorophenyl)phenoxymethyl]tetrahydro-2H-pyran-2-one

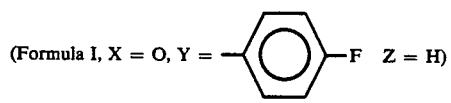

is obtained from the phenol III, (Example 3.2) analogously to Examples 1.6 to 1.9. Colorless solid, melting point 190°-192° C.

$^1$H-NMR(CDCl$_3$, 270 MHz): δ 1.31 (6H,2xd), 1.72-1.95 (3H,m), 2.66 (2H,AB of ABX), 3.47 (1H,hept.), 3.59 (2H,AB of ABX), 4.40 (1H,m), 4.70 (1H,m), 7.12 (4H,m), 7.28 (1H,d), 7.42 (1H,d), 7.55 (4H,m).

MS (DCI): m/e=452 (M$^{30}$ ), 437 (M+-CH$_3$), 129

IR (KBr): 348 (OH), 1715 (C=O), 1510, 1255, 1220, 1200, 1160, 830 cm$^{-1}$

EXAMPLE 4

Synthesis of 4(R)-hydroxy-6(S)-[(2-isopropl-4-phenyl-6-p-fluorophenyl)-phenoxymethyl]tetrahydro-2H-pyran-2-one (Formula I, X=O, Y=phenyl, Z=H)

EXAMPLE 4.1

2-Isopropyl-4-phenylnitrobenzene (Formula IX)

The Grignard solution obtained from 30.7 g (0.25 mole) of 2-bromopropane and 5.85 g (0.24 mole) of magnesium filings in 300 ml of absolute tetrahydrofuran is added dropwise to a solution of 20.0 g (0.1 mole) of 4-nitrobiphenyl VIII in 400 ml of absolute tetrahydrofuran at −70° C. under nitrogen in the course of 3 hours. The mixture is stirred at −70° C. for a further hour (thin-layer chromatography: VIII completely reacted) and a solution of 22.7 g (0.1 mole) of 2,3-dichloro-5,6-dicyano-p-benzoquinone (DDQ) in 200 ml of absolute tetrahydrofuran is then rapidly added dropwise at −40° C. The mixture is allowed to warm to room temperature and is stirred for a further hour and poured onto 1.2 l of water. The tetrahydrofuran is stripped off in vacuo, the aqueous residue is extracted twice with ethyl acetate and the extracts are washed thoroughly with water, dried and concentrated. Chromatography with cyclohexane/CH$_2$CH$_2$ 4:1 through 1 kg of silica gel gives 8.9 g of the title compound IX as a pale red oil.

$^1$H-NMR(CDCl$_3$): δ 1.37 (6H,d); 3.58 (1H,hept.); 7.36-7.97 (8H,m)

MS (70 eV): m/e=241 (M+), 224, 174, 152

EXAMPLE 4.2

2-Isopropyl-4-phenylaniline (Formula X)

13.1 g (54.3 mmol) of the nitro compound IX from Example 4.1 are dissolved in a solution of 10 g of ammonia in 400 ml of methanol. 10 g of Raney nickel which has been washed three times with methanol are added, under nitrogen. The suspension is shaken at room temperature under normal pressure in a hydrogen atmosphere for 2 hours. The catalyst is filtered off, the filtrate is concentrated and the residue is chromatographed over 400 g of silica gel with 2 l of cyclohexane/toluene 1:2 and then with 5 l of toluene. 11.2 g of the title compound X are obtained as a colorless oil.

$^1$H-NMR(CDCl$_3$): δ 1.33 (6H,d); 3.00 (1H,hept.); 3.45 (2H,s,br.); 6.80 (1H,d); 7.2-7.7 (7H,m)

MS (70 eV): m/e=211 (M+), 196 (M+-CH$_3$)

EXAMPLE 4.3

2-Isopropyl-4-phenylphenol

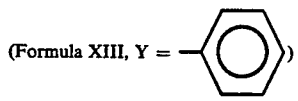

A solution of 4.26 g (62 mmol) of sodium nitrite in 50 ml of water is added to a solution of 11.2 g (53.1 mmol) of the amine X from Example 4.2 in 50 ml of glacial acetic acid at 10° to 12° C. The diazonium salt precipitates. The suspension is difficult to stir. After 5 minutes, the suspension is poured slowly into a boiling solution of 32 ml of concentrated sulfuric acid in 65 ml of water. The mixture is stirred for a further 5 minutes and then cooled and partitioned between toluene/ether and saturated sodium chloride solution. The organic phase is washed twice with saturated NaHCO$_3$ solution and once with sodium chloride solution and then dried and concentrated. gel gives 4.9 g of the title compound XIII as a yellow oil.

$^1$H-NMR(CDCl$_3$): δ 1.30 (6H,d); 3.25 (1H,hept.); 7.1–7.7 (8H,m)

MS (70 eV): m/e=212 (M+), 197 (M+-CH$_3$), 178

EXAMPLE 4.4

2-Isopropyl-4-phenyl-6-bromophenol- (Formula XIV, Y=phenyl)

is obtained analogously to Example 2.2 from the phenol XIII from Example 4.3.

$^1$H-NMR(CDCl$_3$): δ 1.26 (6H,d); 3.40 (1H,hept.); 5.63 (1H,s); 7.2–7.7 (7H,m)

MS (70 eV): m/e=290/292 (M+), 275/277 (M+-CH$_3$), 196, 165

EXAMPLE 4.5

1-Benzyloxy-2-isopropyl-4-phenyl-6-bromobenzene (Formula XV, Y=phenyl)

is obtained analogously to Example 1.3 from the phenol XIV (Example 4.4) as a colorless oil which slowly crystallizes.

$^1$H-NMR(CDCl$_3$): δ 1.24 (6H,d); 3.45 (1H,hept.); 5.05 (2H,s); 6.95–7.70 (12H,m)

MS (70 eV): m/e=380/382 (M+), 91

EXAMPLE 4.6

1-Benzyloxy-2-isopropyl-4-phenyl-6-p-fluorophenyl-benzene (Formula XVIII, Y=phenyl, Z=H)

is obtained analogously to Example 1.4 from the corresponding Grignard compound XVI as a colorless oil which slowly crystallizes.

$^1$H-NMR(CDCl$_3$): δ 1.28 (6H,d); 3.52 (1H,hept.); 5.00 (2H, s); 6.95–7.70 (16H,m)

MS (70 eV): m/e=396 (M+)

EXAMPLE 4.7

2-Isopropyl-4-phenyl-6-p-fluorophenylphenol (Formula III, Y=phenyl, Z=H)

is obtained analogously to Example 1.5 from XVIII from Example 4.6 as a colorless solid.

$^1$H-NMR(CDCl$_3$): δ 1.35 (6H,d); 3.40 (1H,hept.); 5.10 (1H, s,br.); 6.85–7.45 (11H,m)

MS (70 eV): m/e=306 (M+), 291 (M+-CH$_3$)

EXAMPLES 4.8 to 4.11

4(R)-Hydroxy-6(S)-[(2-isopropyl-4-phenyl-6-p-fluorophenyl)phenoxymethyl]tetrahydro-2H-pyran-2-one (Formula I, X=O, Y=phenyl, Z=H)

is obtained from the phenol (Example 4.7) analogously to Examples 1.6 to 1.9. Colorless solid, melting point 184°–187° C.

$^1$H-NMR(CDCl$_3$): δ 1.30 (6H,2xd), 1.7–2.0 (3H,m), 2.65 (2H, m), 3.50 (1H,hept.), 3.60 (2H,m), 4.40 (1H,m), 4.70 (1H,m), 7.1–7.6 (11H,m)

MS (DCI): m/e=434 (M+), 4219 (M+-CH$_3$)

EXAMPLE 5

Synthesis of 4(R)-hydroxy-6(S)-[2-isopropyl-4-cyclohexyl-6-p-fluorophenyl)-phenoxymethyl]tetrahydro-2H-pyran-2-one (Formula I, X=O, Y=cyclohexyl, Z=H)

EXAMPLE 1

2-Isopropyl-4-cyclohexyl-phenol Formula XIII, Y=cyclohexyl)

2.0 g of 5% palladium-on-charcoal suspended in 50 ml of ethyl acetate are shaken at room temperature in a hydrogen atmosphere for 30 minutes. A solution of 31.2 g (0.1 mole) of the phenol XIII from Example 4.3 in 250 ml of ethyl acetate is added, with exclusion of oxygen, and the mixture is shaken at 50° C under a hydrogen pressure of 5 kg/cm$^2$ for 5 hours. The course of the reaction can be monitored by gas chromatography [1 m of SP 1000 on ®Chromosorb WAW 80 to 100 mesh, 220° C., 1.0 kg/cm$^2$ of N$_2$ carrier gas, t$_{ret}$: XIII

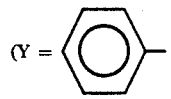

starting compound) 13.8 minutes, product XIII

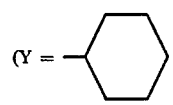

cyclohexyl): 4.6 minutes].

The gas chromatography analysis shows that about 90 of XIII (Y=cyclohexyl) and several by-products, no more than 3% of any, are formed. The catalyst is filtered off and the residue is recrystallized from cyclohexane. 25.0 g of the title compound XIII are obtained as a colorless solid.

$^1$H-NMR(CDCl$_3$): δ 0.8–1.2 (10H,m); 1.25 (6H,d); 3.00 (1H,m); 3.11 (1H,hept.); 4.24 (1H,s,br.); 6.50–7.10 (3H,m)

MS (70 eV): m/e=218 (M+), 203 (M+-CH$_3$)

EXAMPLE 5.2

2-Isopropyl-4-cyclohexyl-6-iodophenol (Formula XIX, Y=cyclohexyl)

is obtained analogously to Example 2.3 from the phenol XIII from Example 5.1.

$^1$H-NMR(CDCl$_3$): δ 0.7–1.4 (10,m); 1.26 (6H,d); 3.0–3.1 (2H,m); 4.60 (1H,s,br.); 6.88–7.40 (2H,m)

MS (70 eV): m/e=344 (M+), 329 (M+—CH$_3$)

EXAMPLE 5.3

2-Isopropyl-4-cyclohexyl-6-p-fluorophenylphenol (Formula III, Y=cyclohexyl, Z=H)

is obtained analogously to Example 2.7 from the iodophenol XIX from Example 5.2.

$^1$H-NMR(CDCl$_3$): δ 0.7–1.2 (10h,M); 1.25 (6h,D); 3.0–3.2 (2h,M); 4.90 (1h,S,BR.); 6.9–7.4 (6H,m)

MS (70 eV): m/e=312 (M+), 297 (M+-CH$_3$)

EXAMPLES 5.4 to 5.7

4(R)-Hydroxy-6(S)-[(2-isopropyl-4-cyclohexyl-6-p-fluorophenyl)phenoxymethyl]tetrahydro-2H-pyran-2-one (Formula I, X=O, Y=cyclohexyl, Z=H)

is obtained from the phenol III from Example 5.3 analogously to Examples 1.6 to 1.9. Colorless solid, melting point 158° to 160° C.

$^1$H-NMR(CDCl$_3$): δ 0.8–1.1 (10H,m); 1.2 (6H,d); 1.68 (1H, s,br.); 1.75 (1H,m); 1.90 (1H,m); 2.55–2.70 (2H,m); 3.0–3.2 (2H,m); 3.55 (2H,m); 4.40 (1H,qui); 4.70 (1H,m); 7.0–7.5 (6H,m)

MS (70 eV): m/e=440 (M+)

EXAMPLE 6

Synthesis of
4(R)-hydroxy-6(S)-[(2,4-diisopropyl-6-p-fluorophenyl)-phen-Ylthiomethy-1]tetrahydro-2H-pyran-2-one
(Formula I, X=S, Y=i-Pr, Z=H)

EXAMPLE 6.1

2,4-Diisopropyl-6-p-fluorophenyl N,N-dimethylthiocarbamat 3.6 g of 50% strength sodium hydrdde are suspended in 60 ml of absolute dimethylformamide. 21.76 g (80 mmol, 1 equivalent) of 2,4-diisopropyl-6-p-fluorophenyl-phenol (Example 1.5) are introduced, while cooling with ice. The solution is stirred at room temperature for 30 minutes and cooled to 0° C. A solution of 12.4 g (1.25 equivalents) of dimethylthiocarbamoyl chloride (Aldrich) in 20 ml of dimethylformamide is added and the reaction mixture is stirred at 80°–90° C. for 5 hours. After cooling, the mixture is diluted with 500 ml of ether, washed twice with water and once with potassium bicarbonate solution and dried over magnesium sulfate and the solvent is stripped off The residue is recrystallized from methanol. 25.6 g (yield of 89%) of the title compound are obtained as a solid, melting point 182° C. MS: m/e=359 (M+)

EXAMPLE 6.2

S-[(2,4-Diisopropyl-6-p-fluorophenyl)phenyl]N,N-dimethylthiocarbamate 25.0 g of the thiocarbamate from Example 6.1 were heated at 270°–300° C. under nitrogen for 1 hour. After cooling, the residue was dissolved in the minimum amount of hot nhexane and after addition of active charcoal the mixture was boiled under reflux for 10 minutes and filtered hot. 20.0 g (80% yield) of the title compound crystallize out of the filtrate as colorless needles during slow cooling.

S: m/e=359 (M+)

EXAMPLE 6.3

2,4-Diisopropyl-6-p-fluorophenyl--thiophenol
(Formula III, X=S, Y=i-Pr, Z=H)

A solution of 19.7 g of the thiocarbamate from Example 6.2 in ether is added dropwise to a suspension of 3.2 g of lithium aluminum hydride in absolute ether, while cooling with ice. The mixture is stirred at room temperature for 2 hours and hydrolyzed with 2N sulfuric acid (to pH 3), while cooling with ice. The mixture is extracted several times with ether, the extract is dried over magnesium sulfate and the solvent is stripped off. 16.8 g of the title compound are obtained as a viscous oil.

MS: m/e=288 (M+), 273 (M+—CH$_3$)

EXAMPLE 6.4

6(S)—-[(2,4-Diisopropyl-6-p-fluorophenyl)phenylthiomethyl]-3,4,5,6-tetrahydro-2(R,S)-methoxy-4(R)-(t-butyldiphenylsilyloxy)-2H-pyran (Formula V, X=S, Y=i-Pr, Z=H, R$^7$=t-butyl-diphenylsilyl)

A suspension of 13.8 g (100 mmol) of potassium carbonate, 14.4 g (50 mmol) of the thiophenol from Example 6.3 and 20.4 g (40 mmol) of the lactol ether iodide IV (R$^7$=t-butyl-diphenylsilyl, for the preparation see EP-A 0,216,127) in 300 ml of absolute dimethyl sulfoxide was stirred at 50° C. for 1 hour. Water was added to the cooled reaction mixture and the mixture was extracted three times with ether. The combined organic phases were washed with water and then with saturated sodium chloride solution, dried over magnesium sulfate and concentrated in vacuo. The residue was chromatographed with toluene/ethyl acetate 95:5 over silica gel and gave 21.4 g (80% yield) of the title compound as a colorless viscous oil.

MS (CI): m/e=670 (M+), 613 (M+-tert.-bu)

EXAMPLE 6.5

6(S)-[(2,4-Diisopropyl-6-p-fluorophenyl)phenylthiomethyl]-3,4,5,6-tetrahydro-2(R,S)-hydroxy-4(R)-(t-butyldiphenylsilyloxy)-2H-pyran (Formula VI)

A solution of 20.1 g (30 mmol) of the lactol ether V from Example 6.4 in 2 l of tetrahydrofuran, 1 l of water and 1 l of trifluoroacetic acid was stirred at 50°–60° C. for 1 hour. After cooling to room temperature, 1.5 kg of sodium acetate were added. The organic solvent was stripped off in vacuo. 1 l of saturated sodium chloride solution was added to te aqueous residue and the mixture was extracted several times with ether. The combined organic extracts were washed with water and dried over magnesium sulfate. The ether was stripped off and the residue was chromatographed with cyclohexane/ethyl acetate 4:1 over silica gel. 13.8 g (70% yield) of the title compound were obtained as a colorless viscous oil.

MS(CI): m/e=656 (M+), 638 (M+—H$_2$O), 581 (M+—t—bu—H$_2$O).

EXAMPLE 6.6

6(S)-[(2,4-Diisopropyl-6-p-fluorophenyl)phenylthiomethyl]-3,4,5,6-tetrahydro-4(R)-(t-butyldiphenylsilyloxy)-2H-pyran-2-one (Formula VII)

A solution of 13.0 g (19.8 mmol) of the lactol VI from Example 6.5, 7.4 g (20 mmol) of tetrabutylammonium iodide and 22.5 g (100 mmol) of N-iodosuccinimide in 200 ml of methylene chloride was stirred at room temperature for 12 hours. 500 ml of toluene were added and the methylene chloride was removed in vacuo. The precipitate was filtered off with suction and washed with toluene. The combined filtrates were washed once each time with aqueous sodium thiosulfate solution and saturated sodium chloride solution, dried over magnesium sulfate, filtered and concentrated in vacuo. The residue was chromatographed with toluene/ethyl acetate 10:1 over silica gel. 11.6 g (90% yield) of the title compound were obtained as a colorless viscous oil.

MS (70 eV, 70° C.): m/e=654 (M+), 597 (M+—t—bu)$_{13}$

EXAMPLE 6.7

4(R)-Hydroxy-6(S)-[(2,4-diisopropyl-6-p-fluorophenyl)-phenylthiomethyl]tetrahydro-2H-pyran-2-one Analogously to Example 1.9, 4.9 g (70% yield) of the title compound are obtained as a viscous colorless oil from 11.0 g of the protected lactone (Example 6.6).

$^1$H-NMR(CDCl$_3$): δ 1.25 (12H, 2xd), 1.65 (OH,s,br.), 1.7-1.9 (2H,m), 2.5-2.6 (2H,m), 2.75 (2H,m), 2.90 (1H,hept.), 3.40 (1H, hept.), 4.35 (1H,qui), 4.50 (1H,m), 7.0-7.5 (6H,m).

MS (FAB): m/e=416 (M+)

EXAMPLE 7

Synthesis of 4(R)-hydroxy-6(S)-[(2-isopropyl-4,6-di-p-fluorophenyl)phenylthiomethyl]tetrahydro-2H-pyran-2-one (Formula I, X=S, Y=p-fluorophenyl, Z=H)

The title compound is obtained by converting 2-isopropyl-4,6-di-p-fluorophenyl-phenol (Example 3.2) into 2-isopropyl-4,6-di-p-fluorophenyl-thiophenol analogously to Examples 6.1 to 6.3 and reacting this to give the title compound analogously to Examples 6.4–6.7. Colorless tacky solid which becomes crystalline when washed with n-hexane, melting point >60° C.

$^1$H-NMR(CDCl$_3$): δ 1.3 (6H,d), 1.7-1.95 (3H,m), 2.5-2.7 (2H,m), 2.75 (2H,m), 3.4 (1H,hept.), 4.4 (1H,m), 4.6 (1H,m), 7.0-7.5 (10H,m).

MS (FAB): m/e=468 (M+), 453 (M+—CH$_3$)
IR (KBr): 3480 (OH), 1715 (C=O)

EXAMPLE 8

Preparation of the sodium salts of the open-chain dihydroxycarboxylic acids (Formula II, sodium salt) from the lactones of the formula I

EXAMPLE 8a

Sodium 3(R),5(S)-dihydroxy-6-[2-(4-fluorophenyl)-4,6-diisopropylphenoxy]-hexanoate 17.7 ml of 1N sodium hydroxide solution are rapidly added dropwise to a solution of 7.0 g (17.5 mmol) of the lactone from Example 1.9 in 800 ml of absolute ethanol, while cooling with ice. The mixture is stirred for 5 minutes, while cooling with ice, and then at room temperature for 2 hours. According to thin-layer chromatography, the starting material has reacted completely. The solvents are stripped off in vacuo at a bath temperature of 30° C. The residue is twice dissolved in ether and the solution is concentrated to dryness each time, the residue is then dissolved in ether and the solution is concentrated to dryness in vacuo. The residue is suspended in toluene and the suspension is concentrated to dryness in vacuo. The residue is stirred with n-pentane and then filtered off with suction and dried under a high vacuum over phosphorus pentoxide and potassium hydroxide lozenges. 6.25 g of the title compound are obtained as a colorless amorphous powder. Concentration of the pentanecontaining mother liquor gives a further 0.43 g of amorphous product. Melting point 240–244° C. (decomposition). The decomposition point depends on the rate of heating up.

EXAMPLE 8b

Sodium 3(R),5(S)-dhydroxy-6-[2-isopropyl-4-tert.-butyl6-(4-fluorophenyl)phenoxy]-hexanoate is obtained analogously to Example 8a from the lactone from Example 2.11. Colorless powder, melting point 256°–258° C. (decomposition)

EXAMPLE 8c

Sodium 3(R),5(S)-dihydroxy-6-[2-isopropyl-4,6-bis-(4fluorophenyl)phenoxy]-hexanoate is obtained analogously to Example 8a from the lactone from Example 3.6. Colorless powder, melting point 235-237° C (decomposition)

EXAMPLE 8d

Sodium 3(R),5(S)-dihydroxy-6-[2-isopropyl-4-phenyl-6-(4-fluorophenyl)phenoxy]-hexanoate is obtained analogously to Example 8a from the lactone from Example 4.11. Colorless powder, melting point 238°–240° C. (decomposition)

EXAMPLE 8e

Sodium 3(R),5(S)-dihydroxy-6-[2-isopropyl-4-cyclohexyl6-(4-fluorophenyl)phenoxy]-hexanoate is obtained analogously to Example 8a from the lactone from Example 5.7. Colorless powder, melting point 230°–233° C. (decomposition)

EXAMPLE 8f

Sodium 3(R),5(S)-dihydroxy-6-[2-(4-fluorophenyl)-4,6-diisopropyl-thiophenoxy]-hexanoate is obtained analogously to Example 8a from the lactone from Example 6.7. Colorless powder, melting point 230°–234° C. (decomposition)

EXAMPLE 8g

Sodium 3(R),5(S)-dihydroxy-6-[2-isopropyl-4,6-bis-(4-fluorophenyl)-thiophenoxy]-hexanoate is obtained analogously to Example 8a from the lactone from Example 7.

We claim:

1. A 6-phenoxymethyl-4-hydroxy-tetrahydro-pyran-2-one and 6-thiophenoxymethyl-4-hydroxy-tetrahydropyaan-2-one of the formula I or a corresponding open-chain dihydroxycarboxylic acid of the formula II

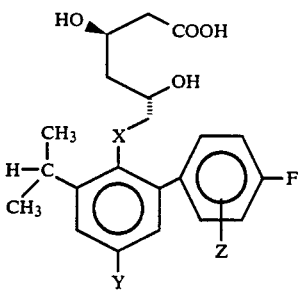

in which
X is oxygen or sulfur,
Y is
a) a straight-chain or branched alkyl radical having 3 to 12 carbon atoms or
b) cycloalkyl having 3 to 8 carbon atoms or a phenyl radical which can be substituted in the nucleus by 1 to 3 substituents from the group comprising comprising halogen, trifluoromethyl and/or alkyl or alkoxy having in each case 1 to 4 carbon atoms and
Z is hydrogen or a straight-chain or branched alkyl radical having 1 to 4 carbon atoms, or a pharmacologically tolerated salt thereof with a base or a pharmacologically tolerated ester thereof.

2. A compound as claimed in claim 1, in which, in the formula I or II
X is oxygen
Y is isopropyl, tert.-butyl, cyclohexyl, phenyl or p-fluorophenyl and
Z is hydrogen.

3. A pharmaceutical preparation which contains a compound as claimed in claim 1 together with an inert carrier.

4. A method for the prophykaxus and therapy or arteriosclerosis and hypercholesterolemia which comprises administering an effective amount of the a compound of formula I or II or said salt or ester thereof as claimed in claim 1.

* * * * *

UNITED STATES PATENT AND TRADEMARK OFFICE
CERTIFICATE OF CORRECTION

PATENT NO. : 5,166,171
DATED : November 24, 1992
INVENTOR(S) : Heiner Jendralla, et. al.

It is certified that error appears in the above-indentified patent and that said Letters Patent is hereby corrected as shown below:

Title page, item [54], Title should read as follows:
--6-PHENOXYMETHYL-4-HYDROXYTETRAHYDROPYRAN-2-ONES AND 6-THIOPHENOXYMETHYL-4-HYDROXYTETRAHYDROPYRAN-2-ONES AND THE CORRESPONDING DIHYDROXYCARBOXYLIC ACID DERIVATIVES, SALTS AND ESTER, AND THEIR USE IN TREATING HYPERCHOLESTEROLEMIA--

Title page, item [54], Title, line 7, delete "and" (second occurrence), should read --and their use--.
Title page, item [57], Abstract, line 8, after "thiophenols" insert --.--.
col. 2, first line Beneath Formula II, "and" (second occurrence) should read --or--.
col. 2, third line Beneath formula II "and" should read --or--.

Claim 1, column 30, lines 54-55, "pyaan-2one" should read --pyran-2-one--.

Claim 1, column 32, line 1, delete, "comprising" (second occurence).

Claim 4, column 32, line 18, "prophykaxus" should read --prophylaxis--.

Claim 4, column 32, line 18, "or" should read --of--.

UNITED STATES PATENT AND TRADEMARK OFFICE
CERTIFICATE OF CORRECTION

PATENT NO. : 5,166,171

DATED : November 24, 1992

INVENTOR(S) : Heiner Jendralla, et. al.

It is certified that error appears in the above-indentified patent and that said Letters Patent is hereby corrected as shown below:

Claim 4, column 32, line 18, "or" should read --of--.

Signed and Sealed this

Fifth Day of April, 1994

*Attest:*

BRUCE LEHMAN

*Attesting Officer*     *Commissioner of Patents and Trademarks*